(12) United States Patent
Motoyama et al.

(10) Patent No.: US 11,490,801 B2
(45) Date of Patent: Nov. 8, 2022

(54) ENDOSCOPE WITH EXTREMELY SMALL DIAMETER

(71) Applicants: THE YOSHIDA DENTAL MFG. CO., LTD., Tokyo (JP); Osamu Motoyama, Tokyo (JP)

(72) Inventors: Osamu Motoyama, Tokyo (JP); Hideki Mogi, Tokyo (JP); Mari Ito, Tokyo (JP); Satoru Kumachi, Tokyo (JP)

(73) Assignees: THE YOSHIDA DENTAL MFG. CO., LTD., Tokyo (JP); Osamu Motoyama, Tokyo (JP)

( * ) Notice: Subject to any disclaimer, the term of this patent is extended or adjusted under 35 U.S.C. 154(b) by 715 days.

(21) Appl. No.: 16/480,629

(22) PCT Filed: Nov. 15, 2017

(86) PCT No.: PCT/JP2017/041042
§ 371 (c)(1),
(2) Date: Jul. 24, 2019

(87) PCT Pub. No.: WO2018/139014
PCT Pub. Date: Aug. 2, 2018

(65) Prior Publication Data
US 2019/0350450 A1 Nov. 21, 2019

(30) Foreign Application Priority Data
Jan. 25, 2017 (JP) .............................. JP2017-011276

(51) Int. Cl.
*A61B 1/247* (2006.01)
*A61B 1/04* (2006.01)
(Continued)

(52) U.S. Cl.
CPC .............. *A61B 1/247* (2013.01); *A61B 1/005* (2013.01); *A61B 1/04* (2013.01); *A61B 1/07* (2013.01);
(Continued)

(58) Field of Classification Search
CPC ........... A61B 1/247; A61B 1/005; A61B 1/04; A61B 1/07; A61B 1/00135; A61B 1/00089; A61B 1/00154
See application file for complete search history.

(56) References Cited

U.S. PATENT DOCUMENTS 4,258,721 A * 3/1981 Parent ................ A61B 1/00108
604/26
4,947,245 A    8/1990 Ogawa et al.
(Continued)

FOREIGN PATENT DOCUMENTS

CN    106037620 A    10/2016
EP    0343558 A1    11/1989
(Continued)

OTHER PUBLICATIONS

Machine language translation of JP 02-104006 U, Aug. 17, 1990 (Year: 1990).*
(Continued)

*Primary Examiner* — John P Leubecker
(74) *Attorney, Agent, or Firm* — Grumbles Law PLLC; Brittany Nanzig (57) ABSTRACT

An extremely small diameter endoscope includes comprises: an endoscope body having a distal end nozzle; an imaging unit disposed in the endoscope body and adapted for capturing an image; an endoscope insertion part having a proximal end portion and a projection end portion, the proximal end portion connected to the imaging unit, the endoscope insertion part passing through the distal end
(Continued)

nozzle, the projection end portion to be positioned in a root canal of a tooth or in a periodontal pocket; and endoscope insertion part insertion means adapted for inserting the endoscope insertion part into an observation portion in the root canal of the tooth or in the periodontal pocket with an end portion of the distal end nozzle kept abutted against a surrounding portion of the observation portion.

10 Claims, 10 Drawing Sheets

(51) Int. Cl.
    *A61B 1/00*            (2006.01)
    *A61B 1/005*          (2006.01)
    *A61B 1/07*            (2006.01)

(52) U.S. Cl.
    CPC ....... *A61B 1/00135* (2013.01); *A61B 1/00154* (2013.01)

(56) References Cited

U.S. PATENT DOCUMENTS

| | | | |
|---|---|---|---|
| 5,230,621 A | | 7/1993 | Jacoby |
| 5,328,365 A | | 7/1994 | Jacoby |
| 2004/0249424 A1* | 12/2004 | Luloh | .................... A61B 90/36 |
| | | | 607/92 |
| 2005/0154379 A1* | 7/2005 | McGowan | ............. A61B 18/22 |
| | | | 606/4 |
| 2007/0249899 A1* | 10/2007 | Seifert | ................. A61B 1/0004 |
| | | | 600/176 |
| 2010/0047733 A1* | 2/2010 | Nahlieli | ............. A61B 1/00167 |
| | | | 433/29 |
| 2015/0216418 A1* | 8/2015 | Ammon | ............... A61B 5/0088 |
| | | | 433/29 |
| 2018/0235441 A1* | 8/2018 | Huang | ............... A61B 1/00135 |

FOREIGN PATENT DOCUMENTS

| | | |
|---|---|---|
| JP | H02-104006 U | 8/1990 |
| JP | 2004065623 A | 3/2004 |
| JP | 2011072719 A | 4/2011 |
| JP | 2012005643 A | 1/2012 |
| JP | 5391019 B2 | 1/2014 |
| WO | 9312732 A1 | 7/1993 |

OTHER PUBLICATIONS

Extended European Search Report for European Application No. 17893642.3; dated Jan. 17, 2020; date of filing: Nov. 15, 2017; 10 pp.

First Office Action for Chinese Application No. 201780084030.7; dated Apr. 8, 2021; date of filing: Jan. 25, 2017; 7 pp.

\* cited by examiner

When capturing a root canal image

ENDOSCOPE WITH EXTREMELY SMALL DIAMETER

TECHNICAL FIELD

The present invention relates to an extremely small diameter endoscope, and specifically to an extremely small diameter endoscope for inspecting and imaging the interior of the root canal of a tooth or the interior of a periodontal pocket.

BACKGROUND ART

In the field of dental treatment, it is most important to understand the shape and condition of the interior of a root canal in the case of endodontic treatment and understand the shape and condition of the interior of a periodontal pocket in the case of periodontal disease treatment, in order to diagnose the presence or absence of source of infection from contaminants such as bacterium, which is a pathologic cause, or in order to diagnose a tooth root fracture or the like. In addition, it is also most important to remove contaminants as much as possible. However, in some circumstances, such important therapeutic treatments are performed blindly especially in endodontic treatments. In recent years, surgical microscopes have begun to be widely used and observation of the interior of a root canal has become easier than before. However, the root canal often curves as it extends, and may have a blind spot that cannot be observed using those surgical microscopes.

An example of this type of root canal imaging instrument is the intraoral scope proposed in Patent Literature 1. This intraoral scope includes a hand piece and a chip insertably connected to the hand piece in an attachable and detachable manner. The hand piece has a light source and the chip has a light guide and an image guide. The light guide receives light from the light source and guides the received light to a distal end of the chip to emit the light forward from the distal end. The image guide transmits an image of a portion irradiated with the light from the light guide. The hand piece further has imaging means for capturing the image transmitted via the image guide. The chip is constituted by a guide tube through which the light guide and the image guide are inserted. A distal end of the guide tube is inserted into a desired portion inside a root canal to transmit an image ahead of the light guide via the image guide to the hand piece. The instrument further has an attachment that is attached to the distal end portion of the chip in an attachable and detachable manner and is adapted for insertion into a periodontal pocket (gap between a tooth and gum). The attachment has extended portions extending forward in parallel with each other and interposing the guide tube in between. Each of the extended portions has a thickness in a height direction that decreases as it extends forward.

The intraoral scope of Patent Literature 1 is mostly used for observing images of the interior of a periodontal pocket. Moreover, the chip has a complicated structure as follows: the chip is constructed with the guide tube through which the light guide and the image guide are inserted and is provided with an attachment attached to a distal end portion of the chip in an attachable and detachable manner, which attachment is for insertion into a periodontal pocket and has extended portions whose distal end portions each have a gradually decreasing dimension as it extends forward. In addition, the chip does not have a configuration for preventing damages to an endoscope insertion part.

That is, currently, there is no such extremely small diameter endoscope that allows: inserting/removing a distal end portion of an endoscope insertion part with an extremely small-diameter for capturing images into/from the interior of the root canal of a tooth or the interior of a periodontal pocket with good operability; capturing images of the interior, including blind spots thereof, of the root canal or the periodontal pocket; and preventing the distal end portion of the endoscope insertion part from being damaged while it is not being used.

PRIOR ART DOCUMENTS

Patent Literatures

Patent Literature 1: U.S. Pat. No. 5,391,019

SUMMARY OF THE INVENTION

Problems to be Solved by the Invention

The present invention has been made in view of the above-described circumstances. The present invention provides an extremely small diameter endoscope with an endoscope body provided with an endoscope insertion part insertion means that allows insertion of an endoscope insertion part for capturing images into the interior of a root canal or a periodontal pocket with a simplified, easy operation, to improve operability of introducing the endoscope insertion part into the interiors of the root canal and the periodontal pocket. The extremely small diameter endoscope has a function of preventing damages to the endoscope insertion part while it is not being introduced into the root canal or the periodontal pocket.

Means for Solving the Problems

According to a major aspect of the present invention, an extremely small diameter endoscope includes: an endoscope body having a distal end nozzle; an imaging unit disposed in the endoscope body and adapted for capturing an image; an endoscope insertion part comprising a proximal end portion and a projection end portion, the proximal end portion connected to the imaging unit, the endoscope insertion part passing through the distal end nozzle, the projection end portion to be positioned in a root canal of a tooth or in a periodontal pocket; and endoscope insertion part insertion means adapted for inserting the endoscope insertion part into an observation portion in the root canal of the tooth or in the periodontal pocket with an end portion of the distal end nozzle kept abutted against a surrounding portion of the observation portion.

Advantageous Effects of the Invention

The invention according to claim 1 provides an extremely small diameter endoscope that allows, by the endoscope insertion part insertion means, bringing the end portion of the distal end nozzle into abutment with the surrounding portion of the observation portion in the root canal of the tooth or in the periodontal pocket and inserting the endoscope insertion part into the observation portion, and thereby allows capturing an image of the interior, including blind spots thereof, of the root canal or the periodontal pocket while improving operability in introducing the endoscope insertion part into the root canal or the periodontal pocket and allows preventing damages to the endoscope insertion part while it is not being introduced into the root canal or the periodontal pocket.

According to the invention of claim 2, the endoscope insertion part insertion means allows for moving the endoscope insertion part in the endoscope body and the distal end nozzle in conjunction with the imaging unit that is moved forward and backward by an operation of a lever slidably attached to the endoscope body. This structure makes it possible for the extremely small diameter endoscope to capture an image of the interior, including blind spots thereof, of the root canal or the periodontal pocket while improving operability in introducing the endoscope insertion part into the root canal or the periodontal pocket and prevent the endoscope insertion part from being damaged while it is not being introduced into the root canal or the periodontal pocket.

According to the invention of claim 3, in the extremely small diameter endoscope described in claim 1 or 2, the distal end nozzle is made of a hard material and the endoscope insertion part has a mantle made of a flexible, elastic material. With this structure of the extremely small diameter endoscope, the endoscope insertion part insertion means can be operated to introduce/withdraw the endoscope insertion part into/from the interior of the root canal or the periodontal pocket with good operability.

According to the invention of claim 4, in the extremely small diameter endoscope described in any one of claims 1 to 3, the distal end nozzle has a projection end portion at which an ingress/egress guiding abutment piece is formed in a substantially spoon-like shape or a substantially scoop-like shape, and the distal end nozzle is adapted to allow the endoscope insertion part to be moved along an inner surface of the ingress/egress guiding abutment piece. With this structure of the extremely small diameter endoscope, the endoscope insertion part can be smoothly introduced into or withdrawn from the interior of the root canal or the periodontal pocket while moving the endoscope insertion part with good operability.

According to the invention of claim 5, in the extremely small diameter endoscope described in claim 4, the distal end nozzle including the ingress/egress guiding abutment piece is curved in a shape suitable for observation. With this structure of the extremely small diameter endoscope, the endoscope insertion part can be introduced into or withdrawn from the interior of the root canal or the periodontal pocket with good operability in a state where the endoscope insertion part fits the shape of the root canal or the periodontal pocket.

According to the invention of claim 6, in the extremely small diameter endoscope described in any one of claims 1 to 5, the extremely small diameter endoscope further includes a distal end nozzle holding sleeve that holds the distal end nozzle on the endoscope body. The distal end nozzle holding sleeve is configured to be attachable to and detachable from the endoscope body. With this structure of the extremely small diameter endoscope, the distal end nozzle can be simply and easily replaced by detaching and attaching the distal end nozzle holding sleeve.

According to the invention of claim 7, the distal end nozzle has an expansion-contraction structure such that: the distal end nozzle shrinks or moves to increase an amount of projection of an end portion of the endoscope insertion part from an end portion of the distal end nozzle by bringing the end portion of the distal end nozzle into abutment with a surrounding region of an entrance to the root canal or the periodontal pocket; and the projection is eliminated by causing the end portion of the distal end nozzle to expand by releasing the abutment of the end portion of the distal end nozzle with the surrounding region of the entrance to the root canal or the periodontal pocket. This structure of the extremely small diameter endoscope allows capturing an image of the interior, including blind spots thereof, of the root canal or the periodontal pocket while improving operability in introducing the endoscope insertion part into the root canal or the periodontal pocket and preventing damage to the endoscope insertion part while it is not being introduced into the root canal or the periodontal pocket.

According to the invention of claim 8, the distal end nozzle includes an expansion-contraction member that constitutes a part or the whole of the distal end nozzle. Bringing the distal end nozzle into abutment with the surrounding region of the entrance to the root canal or the periodontal pocket causes the expansion-contraction member to shrink and thus causes the endoscope insertion part to come out from the distal end nozzle; and releasing the abutment between the distal end nozzle and the surrounding region of the entrance to the root canal or the periodontal pocket causes the expansion-contraction member to expand and thus causes the endoscope insertion part to be housed in the distal end nozzle. This structure makes it possible for the extremely small diameter endoscope to capture an image of the interior, including blind spots thereof, of the root canal or the periodontal pocket while improving operability in introducing the endoscope insertion part into the root canal or the periodontal pocket and prevent the endoscope insertion part from being damaged while it is not being introduced into the root canal or the periodontal pocket.

The invention of claim 9 can provide an extremely small diameter endoscope that provides the same advantageous effects as those of the invention of claim 1 and allows capturing a high-quality, high-brightness image of the root canal or the periodontal pocket.

According to the invention of claim 10, in the extremely small diameter endoscope described in any one of claims 1 to 9, a general purpose channel with a hollow structure is provided in the endoscope insertion part. This structure of the extremely small diameter endoscope makes it possible to inject lavage fluid and/or drug into an affected part in the interior of the root canal or the periodontal pocket using the general purpose channel, and further provide treatment by irradiating the affected part with laser by inserting a laser fiber into the general purpose channel.

EMBODIMENTS OF INVENTION

In order to achieve the purpose of providing an extremely small diameter endoscope having improved operability of introducing an endoscope insertion part into a root canal or a periodontal pocket and having a function of preventing damage to the endoscope insertion part while it is not being introduced into the root canal or the periodontal pocket, the present invention provides an extremely small diameter endoscope including: an endoscope body having a distal end nozzle; an imaging unit disposed in the endoscope body and adapted for capturing an image; an endoscope insertion part comprising a proximal end portion and a projection end portion, the proximal end portion connected to the imaging unit, the endoscope insertion part passing through the distal end nozzle, the projection end portion to be positioned in a root canal of a tooth or in a periodontal pocket; and endoscope insertion part insertion means adapted for inserting the endoscope insertion part into an observation portion in the root canal of the tooth or in the periodontal pocket with an end portion of the distal end nozzle kept abutted against a surrounding portion of the observation portion, wherein the endoscope insertion part insertion means includes a lever slidably attached to the endoscope body and allows moving the endoscope insertion part in the endoscope body and in the distal end nozzle in conjunction with the imaging unit that is moved forward and backward in the endoscope body by an operation of the lever.

Embodiment

Hereinafter, an extremely small diameter endoscope according to an embodiment of the present invention will be described in detail with reference to the drawings.

As shown in FIGS. 1 to 4, the extremely small diameter endoscope according to the present embodiment has: a distal end nozzle holding sleeve 3 on a distal end side; a cylindrical endoscope body 2 that holds a proximal end portion of a thin, elongated cylindrical distal end nozzle 11 with this distal end nozzle holding sleeve 3, through which distal end nozzle 11 a later-mentioned endoscope insertion part 12 is inserted; an imaging unit 4 arranged in the endoscope body 2 and equipped with an image pickup part 4A, such as a CCD camera module, configured to capture an image of a root canal or a periodontal pocket; an endoscope insertion part 12 having a proximal end portion connected to the imaging unit 4 in the endoscope body 2 and a projection end 12a which is positioned, for example, in a root canal 22 of a later-described tooth 21 when the endoscope insertion part 12 is made to pass through the distal end nozzle holding sleeve 3 and the distal end nozzle 11 in such a way that the projection end 12a comes out forward from a distal end aperture 11b of the distal end nozzle 11; and endoscope insertion part insertion means 6 for bringing an end portion of the distal end nozzle 11 provided on the endoscope body 2 into abutment with a surrounding region (surrounding end surface) of an entrance to the root canal 22 (or an entrance to the later-mentioned periodontal pocket) and inserting the endoscope insertion part 12 into the root canal 22 or the like.

The distal end nozzle holding sleeve 3 is configured to be attachable to and detachable from the endoscope body 2, for example, with a thread engagement structure so that the distal end nozzle 11 can be easily replaced.

In other words, when the distal end nozzle holding sleeve 3 is detached from the endoscope body 2, the distal end nozzle 11 and the distal end nozzle holding sleeve 3 can be drawn out from the endoscope insertion part 12 and then the distal end nozzle 11 can be replaced with another one.

By inserting a freely selected distal end nozzle 11 over the endoscope insertion part 12 and threadedly engaging the distal end nozzle holding sleeve 3 with the endoscope body 2, the distal end nozzle 11 can be fixed in a freely selected orientation by a pressing force from the inner side of the distal end nozzle holding sleeve 3.

Incidentally, the distal end nozzle 11 can be formed integrally with the distal end nozzle holding sleeve 3 and the distal end nozzle holding sleeve 3 can be configured to be replaceable.

The distal end nozzle 11 is formed of a hollow structure using, for example, a material that is strong and less deformable. According to the embodiment, the distal end nozzle 11 is made of a metal material, but is not limited thereto.

The endoscope insertion part 12 has a mantle (corresponding to the guide tube 31 shown in FIG. 12) formed of, for example, an elastic flexible material that can be curved. According to the embodiment, the mantle is made of a metal material but it is not limited thereto. In the present case, for example, an imaging element including a combination of a lens and a CCD element may be arranged at a distal end of the interior of the endoscope insertion part 12. In this case, the imaging unit 4 is equipped with only an image processing circuit.

The endoscope insertion part insertion means 6 includes the imaging unit 4 and has a coupling projection 5a coupled to a peripheral portion of the imaging unit 4, attached to a peripheral portion of the endoscope body 2, and inserted through an elongated hole 2a formed on the endoscope body 2. The endoscope insertion part insertion means 6 further has a lever 5 for, by a sliding operation with a finger, advancing and retreating the endoscope insertion part 12, and, at the same time, advancing and retreating the imaging unit 4 in the endoscope body 2 between a retreat position shown in FIG. 2A and an advance position shown in FIG. 3A (a position such that the distal end portion of the endoscope insertion part 12 does not project from a distal end aperture 11b of the distal end nozzle 11).

Figure 2A:
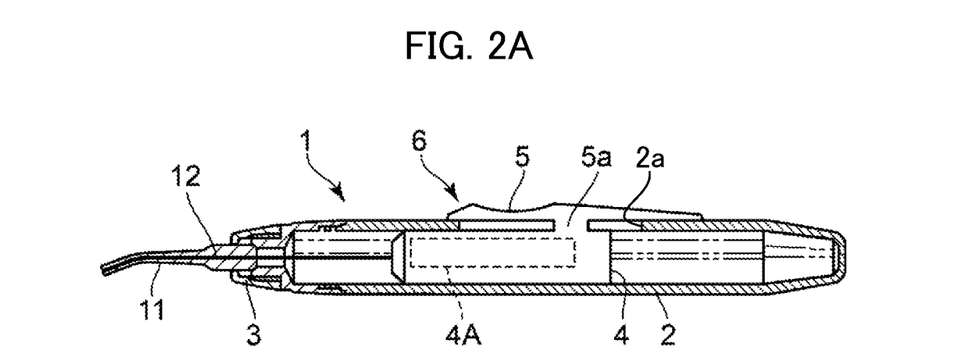
FIG. 2A shows a cross section of the extremely small diameter endoscope (positioned at an imaging unit retreat position) according to the present embodiment.
Figure 2B:
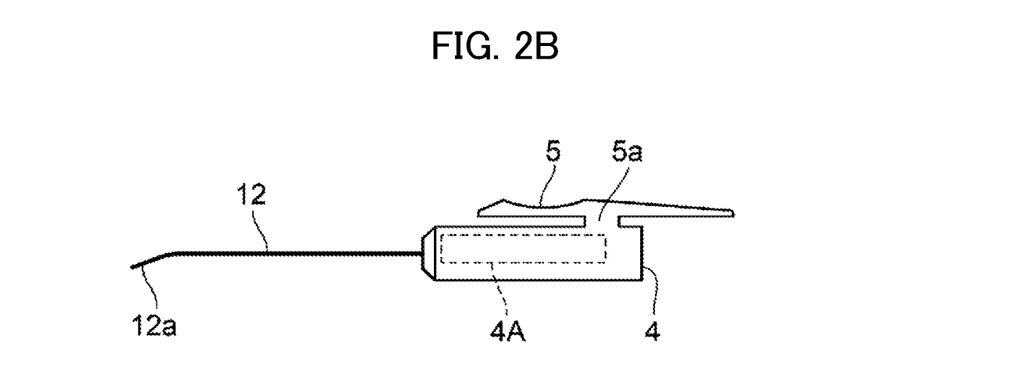
FIG. 2B shows the form of an endoscope insertion part and an imaging unit at this position.
Figure 3A:
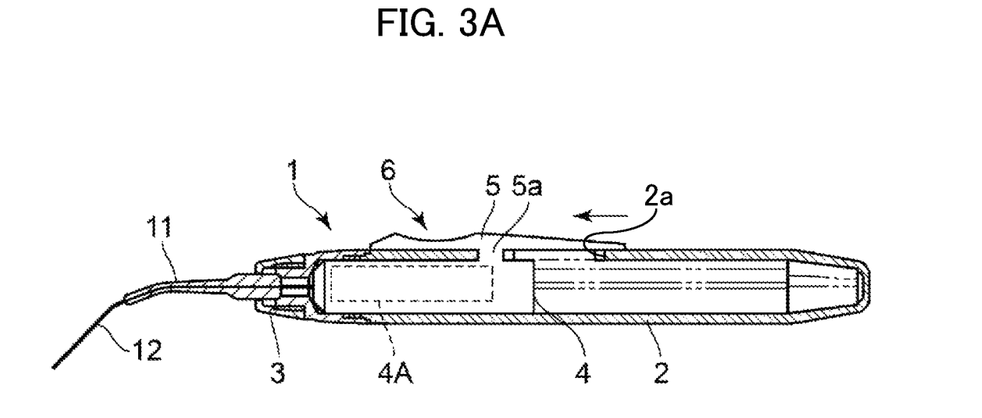
FIG. 3A shows a cross section of the extremely small diameter endoscope (positioned at an imaging unit advance position).
Figure 3B:
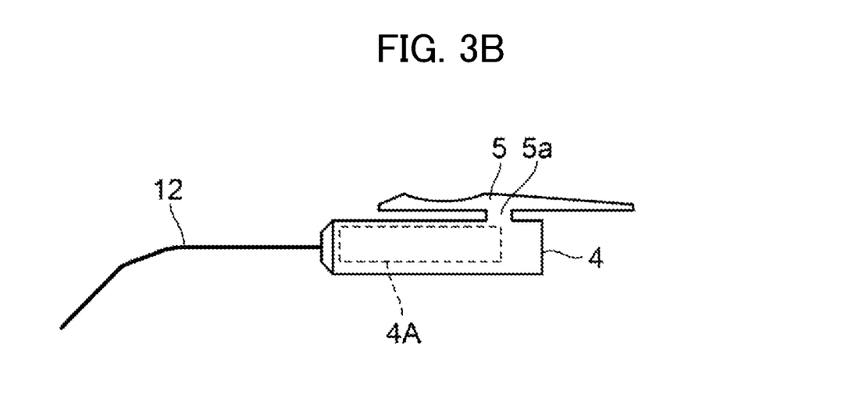
FIG. 3B shows the form of the endoscope insertion part and the imaging unit at this position.

FIG. 2B shows the form of the endoscope insertion part 12 and the imaging unit 4 at the retreat position of the lever 5, and FIG. 3B shows the form of the endoscope insertion part 12 and the imaging unit 4 at the advance position of the lever 5.

The endoscope insertion part insertion means 6 is configured to move the endoscope insertion part 12 in the endoscope body 2, the distal end nozzle holding sleeve 3, and the distal end nozzle 11 in conjunction with the advancing or retreating movement of the imaging unit 4 and further to cause the distal end portion of the endoscope insertion part 12 to come out from and return into an end of the distal end aperture 11b of the distal end nozzle 11.

Incidentally, a root canal image captured by the imaging unit 4 is transmitted via a not-shown signal transmission cable to an image display means to be rendered as an image thereon for observation. Detailed description of this aspect is omitted.

Next, a description will be given of how the extremely small diameter endoscope 1 according to the present embodiment captures an image in the root canal 22 of the tooth 21 with reference to FIG. 4.

Figure 4:
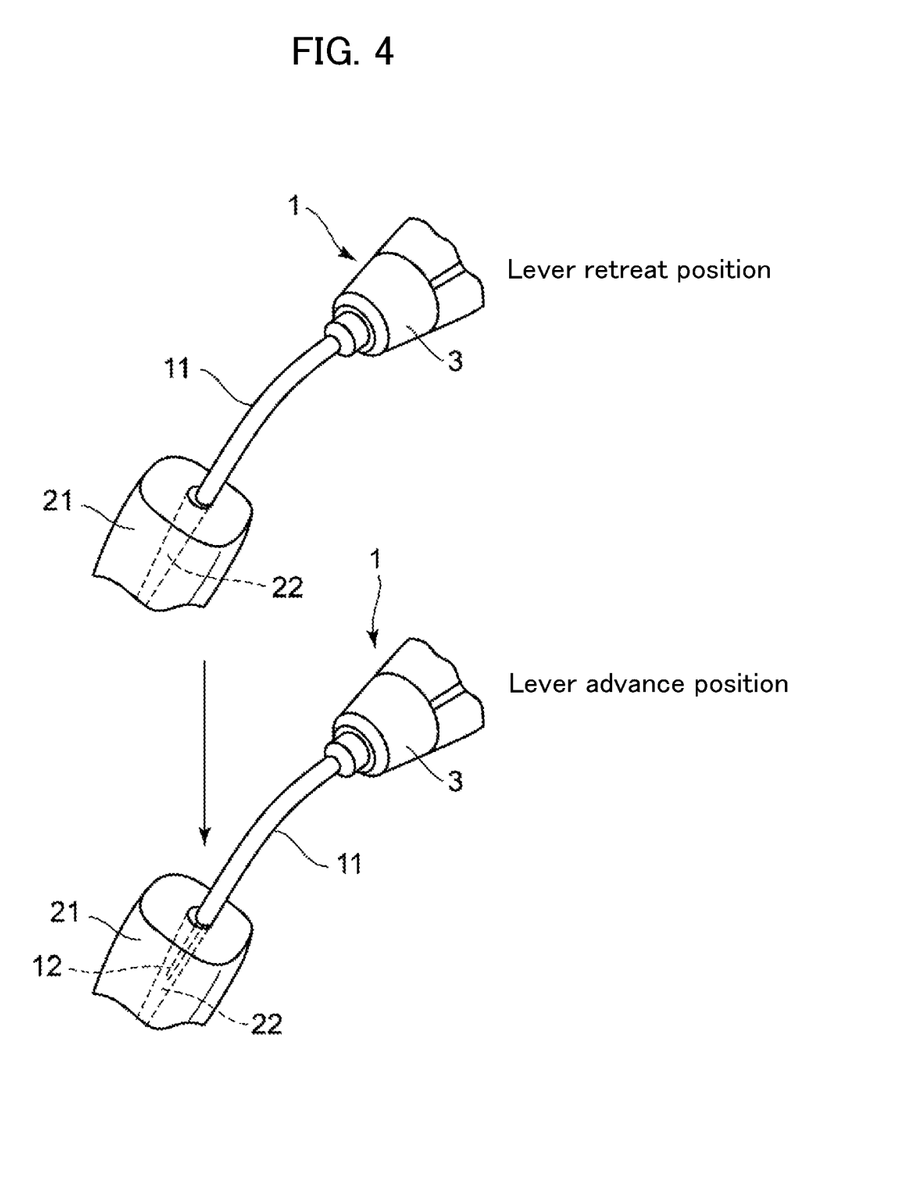
FIG. 4 is an explanatory view of the extremely small diameter endoscope according to the present embodiment, showing the form of the extremely small diameter endoscope when capturing an image of a root canal.

To capture an image of the interior of the root canal 22 of the tooth 21 by the extremely small diameter endoscope 1 according to the present embodiment, first, the lever 5 provided on the extremely small diameter endoscope 1 is brought to the retreat position and the distal end portion of the endoscope insertion part 12 is brought to an end surface of the distal end aperture 11b of the distal end nozzle 11, and then, as shown in the upper half of FIG. 4, the end surface of the distal end aperture 11b of the distal end nozzle 11 is brought into abutment with a surrounding end surface of an entrance to the root canal 22.

Next, as shown in the lower half of FIG. 4, the lever 5 is operated to move the endoscope insertion part 12 to an advance position.

In this way, the distal end portion of the endoscope insertion part 12 enters the interior of the root canal 22 in conjunction with the operation of the lever 5.

The depth to which the distal end portion of the endoscope insertion part 12 penetrates into the interior of the root canal 22 can be controlled by controlling the operation amount of the lever 5.

In this way, it is possible to cause the distal end portion of the endoscope insertion part 12 to reach a desired position in the root canal 22 with a very simple operation with good operability, and observe and capture an image of the vicinity, including blind spots thereof, of the desired position.

When the lever 5 is brought back to the original position, the distal end portion of the endoscope insertion part 12 is at the end surface of the distal end aperture 11b of the distal end nozzle 11, i.e., the projection of the distal end portion from the end surface of the distal end aperture 11b of the distal end nozzle 11 disappears.

With this operation, it is possible to avoid such an undesirable situation that, when the distal end nozzle 11 is brought into or out of the oral cavity, the endoscope insertion part 12 (in particular, the distal end portion of the endoscope insertion part 12) comes into contact with another tooth or the like and is broken.

Next, an extremely small diameter endoscope 1A according to a modification of the present embodiment will be described in detail with reference to FIGS. 5 and 6.

The basic structure of the extremely small diameter endoscope 1A according to the modification is substantially the same as that of the extremely small diameter endoscope 1 of the embodiment. However, the extremely small diameter endoscope 1A adopts an endoscope body 2 with the lever 5 being omitted, and, in place of the endoscope insertion part insertion means 6, has an endoscope insertion part insertion means 6A having a distal end nozzle 11A a part or the whole of which is an expansion-contraction structure formed of, for example, an elastic rubber material in an elongated circular tube shape. The distal end nozzle 11A houses the endoscope insertion part 12 in such a way that the endoscope insertion part 12 can come out from and return into a distal end aperture 11b.

Figure 6:
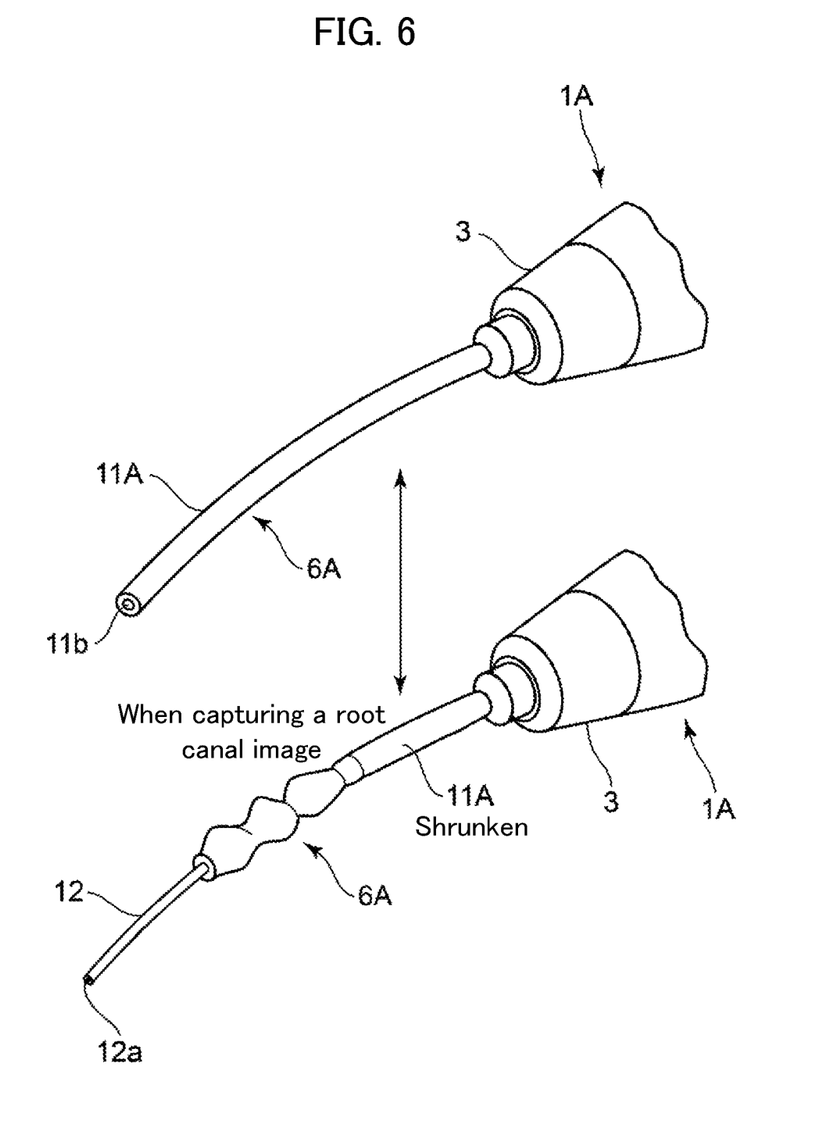
FIG. 6 is an explanatory view of the extremely small diameter endoscope according to the modification of the present embodiment, showing the form of the extremely small diameter endoscope when capturing an image of a root canal.

When capturing an image of the interior of the root canal 22 of the tooth 21, as shown in FIG. 6, an end portion of the distal end nozzle 11A is brought into contact with (brought into abutment with) a surrounding region of an entrance to the root canal 22 to shrink the end portion so as to increase the amount of projection of the endoscope insertion part 12 from the end portion of the distal end nozzle 11A into the root canal 22. Then, the projection of the endoscope insertion part 12 is eliminated by causing the end portion of the distal end nozzle 11A to expand due to its elastic force by releasing the abutment of the end portion of the distal end nozzle 11A with the surrounding region of the entrance to the root canal 22.

In other words, bringing the distal end nozzle 11A into abutment with the surrounding end surface of the entrance to the root canal 22 causes a part or the whole of the distal end nozzle 11a to shrink and thus causes the endoscope insertion part 12 to come out from the distal end nozzle 11A, and releasing the abutment between the distal end nozzle 11A and the surrounding end surface of the entrance to the root canal 22 causes the part or the whole of the distal end nozzle 11a to expand and thus causes the endoscope insertion part 12 to be housed in the distal end nozzle 11A.

Incidentally, in the embodiment shown in FIG. 6, only the distal end portion of the distal end nozzle 11A is shrunken. However, of course, the distal end nozzle 11A may be configured to entirely shrink.

The amount of insertion of the distal end portion of the endoscope insertion part 12 into the root canal 22 can be varied by controlling the abutment force of the end portion of the distal end nozzle 11A applied to the surrounding region of the entrance to the root canal 22.

Even with the extremely small diameter endoscope 1A according to the modification, the distal end portion of the endoscope insertion part 12 can be made to reach a desired position in the root canal 22 with a very simple operation with good operability, and an image can be captured from that position to be observed.

In addition, it is possible to avoid such an undesirable situation that, when the distal end nozzle 11 is brought into or out of the oral cavity, the endoscope insertion part 12 (in particular, the distal end portion of the endoscope insertion part 12) comes into contact with another tooth and is broken.

Figure 7:
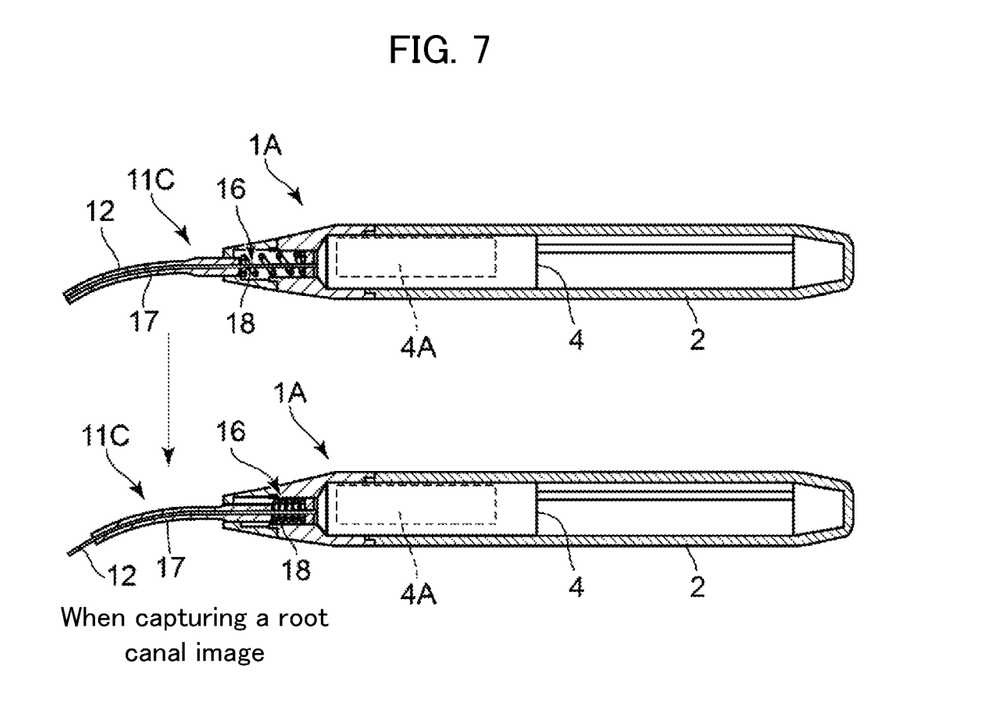
FIG. 7 is a schematic cross-sectional view of the extremely small diameter endoscope according to the modification, showing another expansion-contraction structure of a distal end nozzle of the extremely small diameter endoscope.

FIG. 7 shows a distal end nozzle 11C adopted in place of the distal end nozzle 11A in the extremely small diameter endoscope 1A according to the modification.

This distal end nozzle 11C has: a proximal end portion 16 having a circular cylindrical shape and arranged in the distal end nozzle holding sleeve 3; and a projection nozzle 17 with an elongated, circular tube shape. This distal end nozzle 11C allows the endoscope insertion part 12 connected with the imaging unit 4 to be inserted through the proximal end portion 16 and the projection nozzle 17. The proximal end portion 16 is provided with an expansion-contraction part 18 formed in a coil shape using, for example, a metal material or synthetic resin material.

Even with the extremely small diameter endoscope 1A adopting such a distal end nozzle 11C, utilizing the expansion and contraction of the expansion-contraction part 18, the distal end portion of the endoscope insertion part 12 can be made to reach a desired position in the root canal 22 with a very simple operation with good operability in the same manner as that shown in FIG. 6 and an image can be captured from that position to be observed. Moreover, it is possible to avoid such an undesirable situation that, when the distal end nozzle 11C is brought into or out of the oral cavity, the endoscope insertion part 12 (in particular, the distal end portion of the endoscope insertion part 12) comes into contact with another tooth and is broken.

Next, an extremely small diameter endoscope 1B according to another modification of the present embodiment will be described in detail with reference to FIG. 8.

The basic structure of the extremely small diameter endoscope 1B according to the modification is substantially the same as that of the extremely small diameter endoscope 1 of the embodiment. However, the extremely small diameter endoscope 1B is characterized in further including an illumination light guide 15 with a linear shape. The illumination light guide 15 guides illumination light emitted from a light source part 14 made up of a light-emitting diode or the like and provided along the image pickup part 4A in the imaging unit 4, and emits the illumination light toward the interior of the root canal 22 of the tooth 21 from a position adjacent to the distal end of the endoscope insertion part 12.

As a matter of course, any one of the distal end nozzle 11A and the distal end nozzle 11C can be adopted even in this root canal imaging instrument 1B.

The extremely small diameter endoscope 1B according to the modification can even provide the same effects as those of the above-described extremely small diameter endoscopes 1 and 1A and allows capturing a more bright, high quality image of a root canal by emitting the illumination light from the illumination light guide 15 toward the interior of the root canal 22.

Next, a description will be given of a distal end nozzle 11D that allows the extremely small diameter endoscope 1 of the above-described embodiment to have a function of capturing an image of a periodontal pocket 24 between a gum 23 and a tooth 21, with reference to FIGS. 9, 10A, 10B, and 11A to 11C.

Figure 10A:
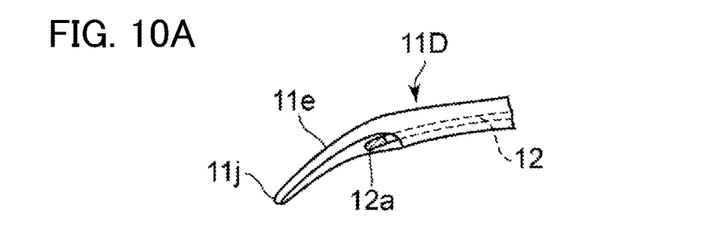
FIGS. 10A and 10B are each a partial perspective view of a distal end nozzle with a straight ingress/egress guiding abutment piece according to the present embodiment as well as the endoscope insertion part.
Figure 10B:
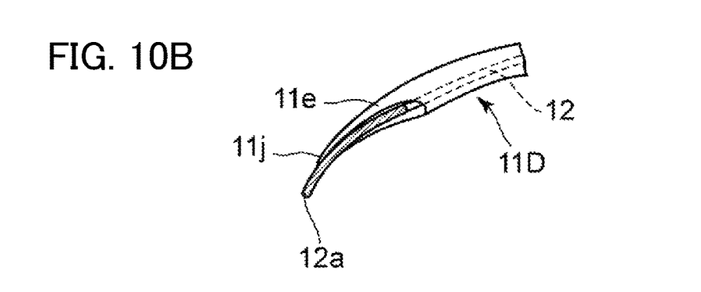

The distal end nozzle 11D has a structure substantially the same as the above-described distal end nozzle 11. However, the distal end nozzle 11D is characterized in including a distal end portion at which a straight ingress/egress guiding abutment piece 11e for the projection end 12a of the endoscope insertion part 12 is formed.

The ingress/egress guiding abutment piece 11e includes an abutment portion 11j for abutting on a periphery region of an opening of the periodontal pocket 24. The abutment portion 11j is a projection end of the distal end nozzle 11D, which projection end is formed by processing the hollow distal end nozzle 11D so as to have a distal end portion substantially having an external shape of a scoop.

That is, the ingress/egress guiding abutment piece 11e guides the projection end 12a of the endoscope insertion part 12 in such a way that, when the state of the projection end 12a of the endoscope insertion part 12 is changed from a state, shown in FIG. 10A, where the projection end 12a of the endoscope insertion part 12 is at a position corresponding to when the lever 5 of the endoscope insertion part insertion means 6 is at the retreat position, to a state, shown in FIG. 10B, where the lever 5 has been operated to move to a position corresponding to an advance position (where the projection end 12a projects further than the abutment portion 11j in an outward direction), the projection end 12a and a part of a portion of the endoscope insertion part 12 that succeeds the projection end 12a (front side in FIG. 10B) are exposed to the outside and the other part of the endoscope insertion part 12 (back side in FIG. 10B) is in contact with an inner periphery surface of the ingress/egress guiding abutment piece 11e.

Figure 9:
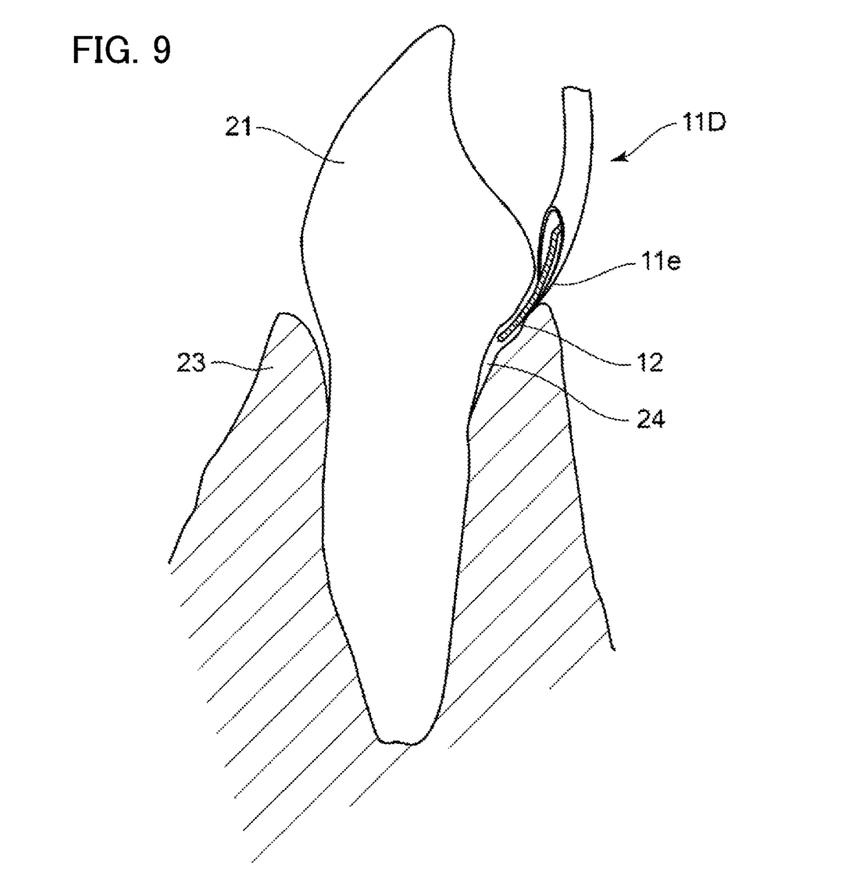
FIG. 9 is a schematic explanatory view of an extremely small diameter endoscope employing a distal end nozzle with an ingress/egress guiding abutment piece of the present embodiment, showing the form of the extremely small diameter endoscope when capturing an image in the interior of a periodontal pocket.

With the extremely small diameter endoscope 1 provided with the distal end nozzle 11D having such a structure, as shown in FIG. 9, it is possible to capture an image of the interior of the periodontal pocket 24 with good operability by inserting the abutment portion 11j into the periodontal pocket 24 in such a way that a space is created in the periodontal pocket 24 and the abutment portion 11j, bringing the abutment portion 11j into abutment with a periphery portion of an observation portion, and operating the lever 5 to move to an advance position so that the projection end 12a of the endoscope insertion part 12 reaches a desired position in the periodontal pocket 24.

In addition, it is possible to avoid such an undesirable situation that, when the distal end nozzle 11D is brought into or out of the oral cavity, the endoscope insertion part 12 (in particular, the projection end 12a of the endoscope insertion part 12) comes into contact with another tooth and is broken.

Figure 11A:
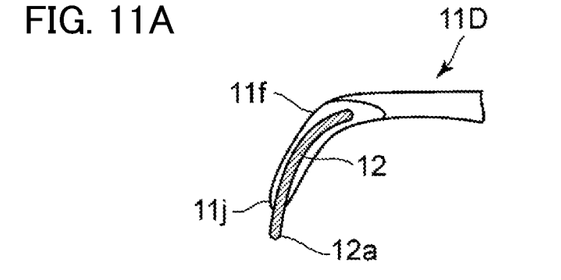
FIGS. 11A, 11B and 11C are partial perspective views of three modifications of the ingress/egress guiding abutment piece according to the present embodiment.
Figure 11B:
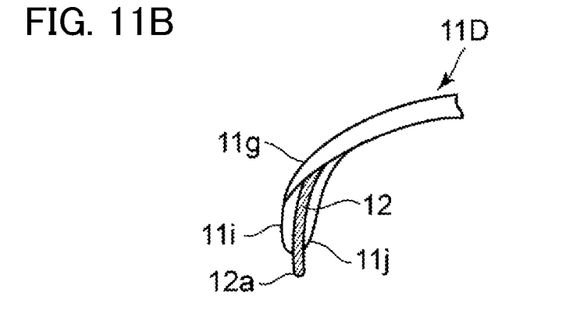
Figure 11C:
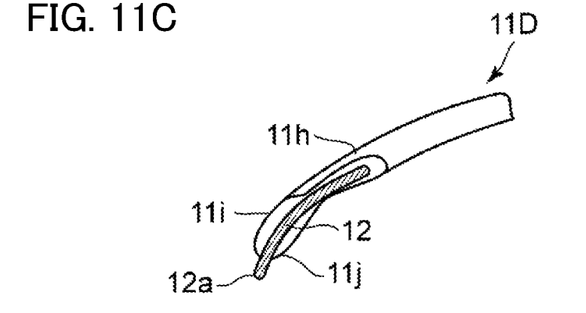

FIGS. 11A to 11C illustrate three embodiments of the modification of the distal end nozzle 11D. FIG. 11A shows a curved ingress/egress guiding abutment piece 11f which can be a replacement for the ingress/egress guiding abutment piece 11e. The curved ingress/egress guiding abutment piece 11f has a distal end portion whose external shape is substantially scoop-shaped and is curved. FIG. 11B shows a curved ingress/egress guiding abutment piece 11g which can be a replacement for the ingress/egress guiding abutment piece 11e. The curved ingress/egress guiding abutment piece 11g has a distal end portion at which a spoon-shaped bulge 11i is formed and the external shape of which is substantially spoon-shaped and is curved. FIG. 11C shows a straight ingress/egress guiding abutment piece 11h which can be a replacement for the ingress/egress guiding abutment piece 11e. The straight ingress/egress guiding abutment piece 11h has a distal end portion at which a spoon-shaped bulge 11i is formed and the external shape of which is substantially spoon-like and is straight.

Even with an extremely small diameter endoscope 1 equipped with the distal end nozzle 11D with any one of the curved ingress/egress guiding abutment piece 11f, the curved ingress/egress guiding abutment piece 11g, and the straight ingress/egress guiding abutment piece 11h, it is possible to provide the same operations and advantageous effects as those provided by the extremely small diameter endoscope 1 equipped with the distal end nozzle 11D having the above-described configuration shown in FIGS. 10A and 10B. In addition, it is further possible to select a distal end nozzle 11D depending on different shapes of the openings of various periodontal pockets 24, to capture an image of a periodontal pocket. It should be noted that each distal end nozzle 11D can be easily exchanged by attaching/detaching the distal end nozzle holding sleeve 3 to/from the endoscope body 2.

Next, another configuration of the endoscope insertion part 12 will be described with reference to FIGS. 12 and 13.

Figure 12:
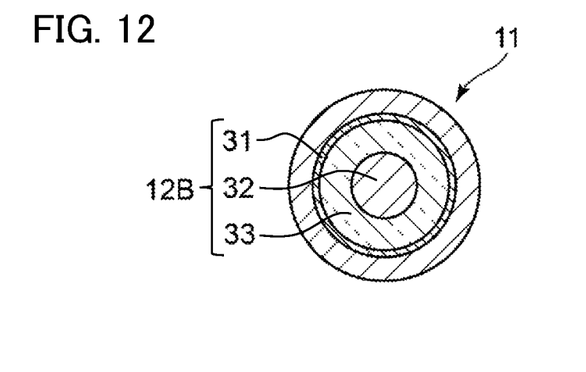
FIG. 12 is a cross-sectional view of an end of another configuration of the endoscope insertion part arranged in the distal end nozzle of the present embodiment.

FIG. 12 shows the configuration of a distal end surface of the distal end nozzle 11, in a hollow portion of which an endoscope insertion part 12B is movably arranged.

The endoscope insertion part 12B includes: a guide tube (mantle, e.g., electroformed tube) 31 slidably in contact with an inner circumference of the hollow portion of the distal end nozzle 11 and having flexibility; a light guide 33 having a circular cylindrical shape and arranged in the guide tube 31 with an outer circumference of the light guide 33 being in contact with an inner circumference of the guide tube 31; and an image guide 32 arranged concentrically with a central portion of this light guide 33 to penetrate therethrough.

The above-described guide tube 31 is made of an elastic material that can be curved. In the configuration example illustrated in FIG. 12, the guide tube 31 is formed of a thin metal material, but it is not limited thereto.

Figure 8:
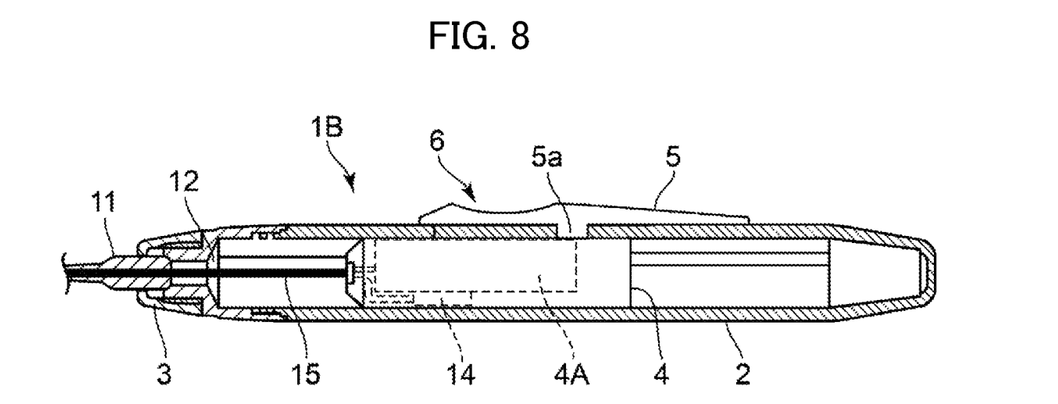
FIG. 8 is a schematic cross-sectional view of an extremely small diameter endoscope according to another modification of the present embodiment.

When an endoscope insertion part 12B having such a configuration is adopted, it is possible to provide the same operations and advantageous effects as those described above for the extremely small diameter endoscope 1B shown in FIG. 8.

Although not illustrated, the endoscope insertion part 12B shown in FIG. 12 may be configured to include, in place of the image guide 32, an extremely small camera, such as a CCD module or the like, and a signal transmission cable. In this case, an image processing unit is used in place of the imaging unit 4 in the endoscope body 2.

The guide tube 31 serves as a guide for protecting the image guide 32 and further the extremely small camera and the signal transmission cable, and for guiding them to an affected part.

Figure 13:
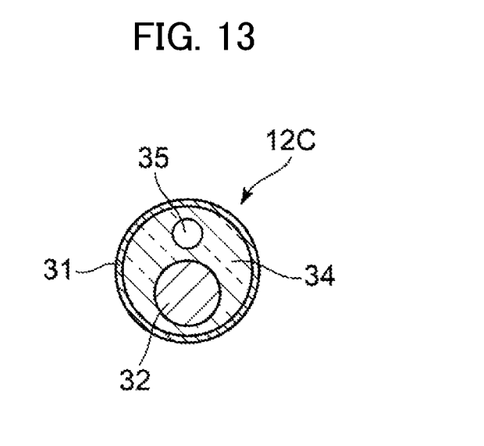
FIG. 13 is a cross-sectional view of an end of yet another configuration of the endoscope insertion part of the present embodiment.

FIG. 13 illustrates an endoscope insertion part 12C having a different configuration from that of the endoscope insertion part 12B. The endoscope insertion part 12C includes: a guide tube (mantle) 31 slidably in contact with an inner circumference of the hollow portion of the distal end nozzle 11 and having flexibility; a light guide 34 arranged in the guide tube 31 with an outer circumference of the light guide 34 being in contact with an inner circumference of the guide tube 31; an image guide 32 disposed to penetrate through the light guide 34; and a general purpose channel (hollow hole) 35 disposed to penetrate through the light guide 34 separately from the image guide 32.

When the endoscope insertion part 12C thus structured is adopted, it is possible to provide the same operations and advantageous effects as those described above for the extremely small diameter endoscope 1B shown in FIG. 8. In addition, as the endoscope insertion part 12C has the general purpose channel 35, it is possible to inject lavage fluid and/or drug into an affected part using the general purpose channel 35 and further treat the affected part with laser irradiation by, although not illustrated, inserting a laser fiber into the general purpose channel 35.

Next, a description will be given of an extremely small diameter endoscope 1C according to another embodiment of the present invention with reference to FIGS. 14, 15A and 15B.

Figure 1:
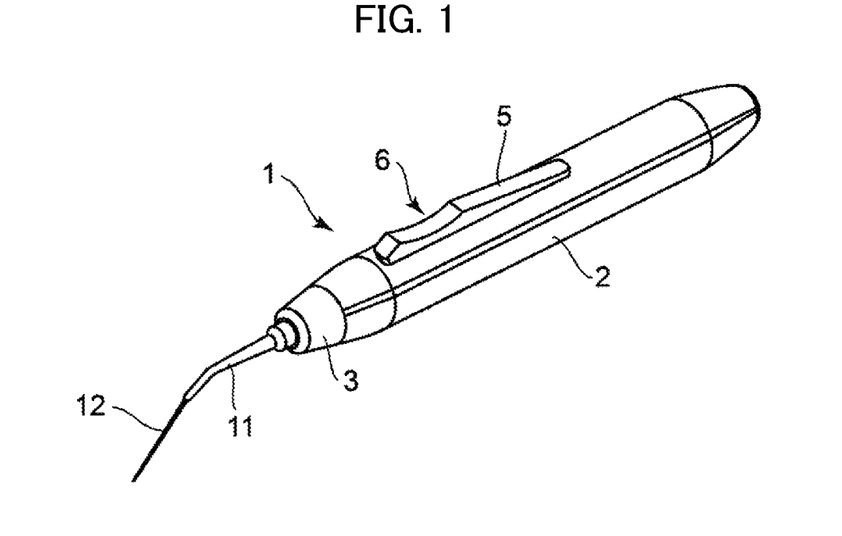
FIG. 1 is an external perspective view of an extremely small diameter endoscope according to an embodiment of the present invention.

As to the extremely small diameter endoscope 1C according to another embodiment, the same elements as in the case of the extremely small diameter endoscope 1 shown in FIG. 1 are given the same reference signs, and their detailed description will be omitted.

The basic structure of the extremely small diameter endoscope 1C according to the embodiment is substantially the same as that of the extremely small diameter endoscope 1 of the embodiment. However, the extremely small diameter endoscope 1C is characterized in that an image processing unit 41 with an image processing circuit 41a is disposed in the endoscope body 2 in place of the imaging unit 4, an endoscope insertion part 42 made up of: a flexible signal transmission cable 43 which has an end portion located in the endoscope body 2 and connected to the image processing unit 41; and an ultra-small size imaging element 44 disposed on a distal end of the signal transmission cable 43 is adopted in place of the endoscope insertion part 12, and the endoscope insertion part insertion means 6 is operated to move the endoscope insertion part 42 in the distal end nozzle 11 in conjunction with the image processing unit 41, so that the ultra-small size imaging element 44 comes out from and returns into the distal end aperture 11b.

Examples of the ultra-small size imaging element 44 include ultra-small size CCD elements and ultra-small size C-MOS elements.

Figure 15A:
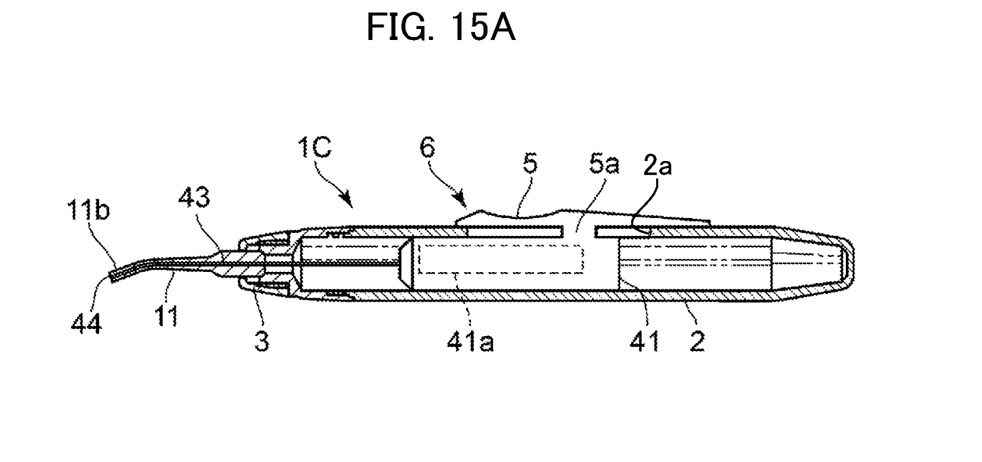
FIG. 15A is a schematic cross-sectional view of an extremely small diameter endoscope (positioned at a lever retreat position) according to another embodiment.
Figure 15B:
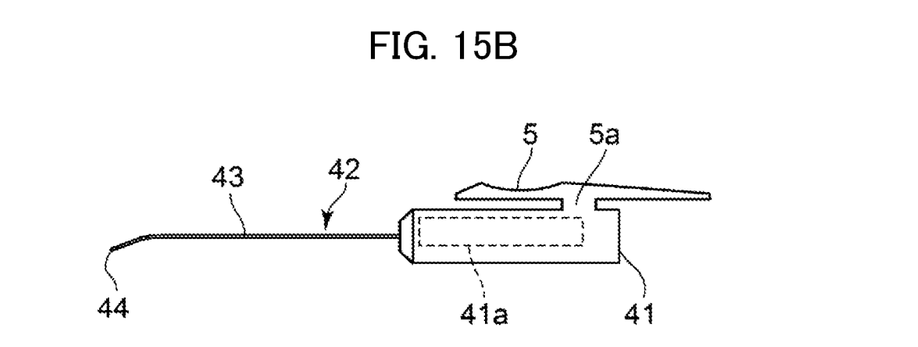
FIG. 15B is a diagram showing the form of the endoscope insertion part and the image processing unit at that position.

It should be noted that FIGS. 15A and 15B illustrate a state where the lever 5 of the endoscope insertion part insertion means 6 is at the retreat position.

The extremely small diameter endoscope 1C according to the embodiment even can provide the same operations and advantageous effects as those described above for the extremely small diameter endoscope 1.

Figure 5:
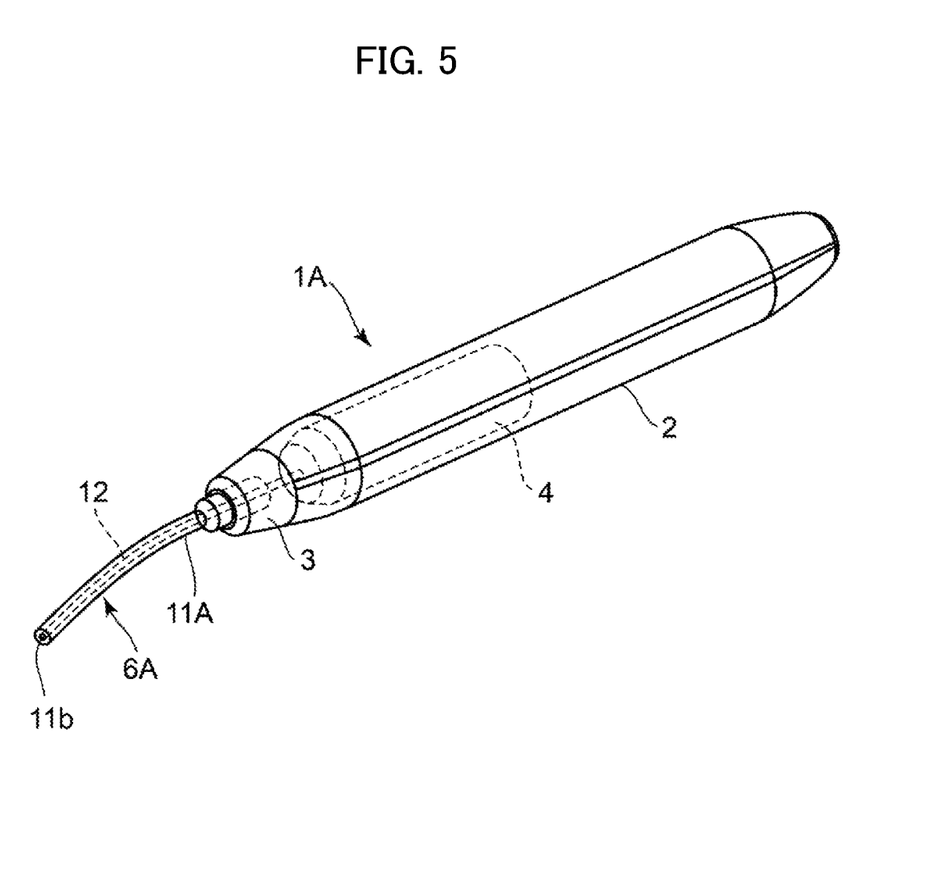
FIG. 5 is an external perspective view of an extremely small diameter endoscope according to a modification of the present embodiment.
Figure 14:
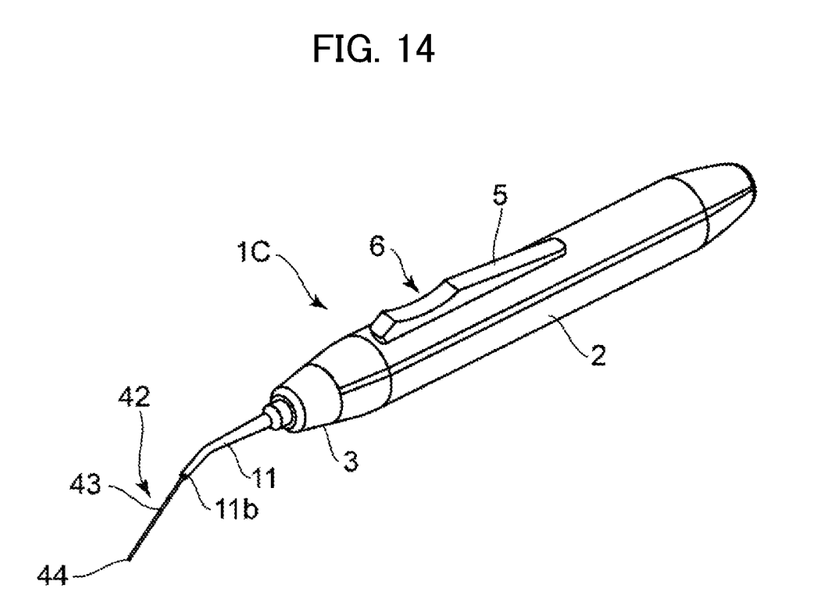
FIG. 14 is an external perspective view of an extremely small diameter endoscope according to another embodiment of the present invention.

It should be noted that the extremely small diameter endoscope 1 shown in FIG. 1 and the like, the extremely small diameter endoscope 1A shown in FIG. 5 and the like, the extremely small diameter endoscope 1B shown in FIG. 8 and the like, and the extremely small diameter endoscope 1C shown in FIG. 14 and the like can be used for capturing an image of the interior of a periodontal pocket 24 in addition to capturing an image of the interior of a root canal 22. In addition, an extremely small diameter endoscope 1 using a distal end nozzle 11D provided with any one of the ingress/egress guiding abutment pieces 11e to 11h can be used for capturing an image of the interior of a root canal 22 in addition to capturing an image of the interior of a periodontal pocket 24.

INDUSTRIAL APPLICABILITY

The present invention is applicable to capturing an image of the interior of a root canal and the interior of a periodontal pocket 24 and further to capturing an image of a treatment part having an affected part in a hole, and thus can be widely used in the medical field.

REFERENCE SIGNS LIST 1 extremely small diameter endoscope
1A extremely small diameter endoscope
1B extremely small diameter endoscope
1C extremely small diameter endoscope
2 endoscope body 2a elongated hole
3 distal end nozzle holding sleeve
4 imaging unit
4A imaging pickup part
5 lever
5a coupling projection
6 endoscope insertion part insertion means
6A endoscope insertion part insertion means
11 distal end nozzle
11A distal end nozzle
11b distal end aperture
11C distal end nozzle
11D distal end nozzle
11e ingress/egress guiding abutment piece
11f curved ingress/egress guiding abutment piece
11g curved ingress/egress guiding abutment piece
11h straight curved ingress/egress guiding abutment piece
11i spoon-shaped bulge
11j abutment portion
12 endoscope insertion part
12a projection end
12B endoscope insertion part
12C endoscope insertion part
14 light source part
15 illumination light guide
16 proximal end portion
17 projection nozzle
18 expansion-contraction part
21 tooth
22 root canal
23 gum
24 periodontal pocket
31 guide tube
32 image guide
33 light guide
34 light guide
35 general purpose channel
41 image processing unit
41a image processing circuit
42 endoscope insertion part
43 signal transmission cable
44 ultra-small size imaging element

What is claimed is:

1. An extremely small diameter endoscope comprising:
an endoscope body having a distal end nozzle;
an imaging unit disposed in the endoscope body and adapted for capturing an image;
an endoscope insertion part comprising a proximal end portion and a projection end portion, the proximal end portion connected to the imaging unit, the endoscope insertion part passing through the distal end nozzle, the projection end portion to be positioned in a root canal of a tooth or in a periodontal pocket; and
endoscope insertion part insertion means adapted for inserting the endoscope insertion part into an observation portion in the root canal of the tooth or in the periodontal pocket with an end portion of the distal end nozzle kept abutted against a surrounding portion of the observation portion,
wherein the endoscope insertion part insertion means includes the imaging unit and a lever extending from the imaging unit and slidably attached to the endoscope body,
wherein the endoscope insertion part insertion means allows for moving the endoscope insertion part in the endoscope body and in the distal end nozzle in conjunction with the imaging unit that is moved forward and backward by an operation of the lever.

2. The extremely small diameter endoscope of claim 1, wherein the distal end nozzle is made of a rigid material, and the endoscope insertion part has a mantle made of an elastic material.

3. The extremely small diameter endoscope of claim 1, wherein the distal end nozzle has a projection end portion at which an ingress/egress guiding abutment piece is formed in a substantially spoon-like shape or a substantially scoop-like shape, and is adapted to allow the endoscope insertion part to be moved along an inner surface of the ingress/egress guiding abutment piece.

4. The extremely small diameter endoscope of claim 1, wherein the extremely small diameter endoscope further comprises a distal end nozzle holding sleeve that holds the distal end nozzle on the endoscope body, the distal end nozzle holding sleeve configured to be attachable to and detachable from the endoscope body.

5. The extremely small diameter endoscope of claim 1, wherein the endoscope insertion part further comprises an illumination light guide that guides illumination light emitted from a light source part provided in the imaging unit.

6. The extremely small diameter endoscope of claim 1, wherein a general purpose hollow channel is provided in the endoscope insertion part.

7. The extremely small diameter endoscope of claim 1, wherein the endoscope insertion part insertion means is configured to allow a user to, by user slide operations of the lever forward and backward, slide the endoscope insertion part insertion means forward and backward in the same directions, to move the endoscope insertion part forward and backward in the endoscope body and in the distal end nozzle in conjunction with the imaging unit and thereby to insert the endoscope insertion part into an observation portion in the root canal of the tooth or in the periodontal pocket with an end portion of the distal end nozzle kept abutted against a surrounding portion of the observation portion.

8. The extremely small diameter endoscope of claim 1, wherein the lever comprises a coupling projection coupled to a peripheral portion of the imaging unit, slidably attached to a peripheral portion of the endoscope body, and inserted through an elongated hole formed on the endoscope body.

9. An extremely small diameter endoscope comprising:
an endoscope body having a distal end nozzle;
an imaging unit disposed in the endoscope body and adapted for capturing an image;
an endoscope insertion part comprising a proximal end portion and a projection end portion, the proximal end portion connected to the imaging unit, the endoscope insertion part passing through the distal end nozzle, the projection end portion to be positioned in a root canal of a tooth or in a periodontal pocket; and
endoscope insertion part insertion means adapted for inserting the endoscope insertion part into an observation portion in the root canal of the tooth or in the periodontal pocket with an end portion of the distal end nozzle kept abutted against a surrounding portion of the observation portion,
wherein the endoscope insertion part insertion means is constituted by the distal end nozzle,
wherein the distal end nozzle comprises an expansion-contraction member through which the endoscope insertion part passes, and wherein the expansion-contraction member is formed of an elastic rubber material in an elongated circular tube shape such that the distal end nozzle shrinks in a longitudinal direction thereof to increase an amount of projection of an end portion of the endoscope insertion part from an end portion of the distal end nozzle by bringing the end portion of the distal end nozzle into abutment with a surrounding region of an entrance to the root canal or the periodontal pocket and such that the projection is eliminated by causing the end portion of the distal end nozzle to expand by releasing the abutment of the end portion of the distal end nozzle with the surrounding region of the entrance to the root canal or the periodontal pocket.

10. The extremely small diameter endoscope of claim 9, wherein the expansion-contraction member constitutes a part or the whole of the distal end nozzle.

* * * * *